(12) United States Patent
Arai et al.

(10) Patent No.: US 9,925,023 B2
(45) Date of Patent: Mar. 27, 2018

(54) IMPLANT OVERDENTURE SYSTEM AND IMPLANT

(71) Applicant: AICHI STEEL CORPORATION, Aichi (JP)

(72) Inventors: Kazuo Arai, Aichi (JP); Yoshinobu Honkura, Aichi (JP); Yasuhiro Takeuchi, Aichi (JP); Rudi Wigianto, Denpasar (ID)

(73) Assignee: AICHI STEEL CORPORATION, Aichi (JP)

( * ) Notice: Subject to any disclaimer, the term of this patent is extended or adjusted under 35 U.S.C. 154(b) by 0 days.

(21) Appl. No.: 14/418,733

(22) PCT Filed: Jun. 4, 2013

(86) PCT No.: PCT/JP2013/065430
§ 371 (c)(1),
(2) Date: Jan. 30, 2015

(87) PCT Pub. No.: WO2014/020985
PCT Pub. Date: Feb. 6, 2014

(65) Prior Publication Data
US 2015/0265379 A1    Sep. 24, 2015

(30) Foreign Application Priority Data
Aug. 1, 2012  (JP) .................................. 2012-171443

(51) Int. Cl.
*A61C 8/00* (2006.01)
*A61C 13/235* (2006.01)

(52) U.S. Cl.
CPC .......... *A61C 8/0081* (2013.01); *A61C 8/0074* (2013.01); *A61C 8/0089* (2013.01); *A61C 8/0095* (2013.01); *A61C 13/235* (2013.01)

(58) Field of Classification Search
CPC ... A61C 13/235; A61C 8/0081; A61C 8/0074; A61C 8/0089; A61C 8/00; A61C 8/0095
(Continued)

(56) References Cited

U.S. PATENT DOCUMENTS

| | | | |
|---|---|---|---|
| 4,508,507 A * | 4/1985 | Jackson | A61C 13/235 433/172 |
| 4,671,768 A * | 6/1987 | Ton | A61C 8/0018 433/173 |

(Continued)

FOREIGN PATENT DOCUMENTS

| | | |
|---|---|---|
| CN | 2216818 Y | 1/1996 |
| CN | 101909542 A | 12/2010 |

(Continued)

OTHER PUBLICATIONS

International Search Report dated Jul. 16, 2013 in PCT/JP13/065430 Filed Jun. 4, 2013.

(Continued)

*Primary Examiner* — Yogesh Patel
(74) *Attorney, Agent, or Firm* — Oblon, McClelland, Maier & Neustadt, L.L.P.

(57) ABSTRACT

An implant overdenture system is used to fix an implant overdenture onto alveolar ridge by the support of implants. The implant overdenture has artificial teeth, a denture base, and magnetic assemblies. The implants each have an implant body and a keeper. A largest circumscribed circle diameter d1 in an outer shape of a surface-to-be-attracted of the keeper is equal to or larger than φ1.8 mm, and a largest diameter d2 of the implant body is equal to or larger than φ1.2 mm and equal to or less than φ3.5 mm, and these largest diameters have a relationship expressed by d1/d2≤1.5.

9 Claims, 14 Drawing Sheets

(58) Field of Classification Search
USPC .................................................. 433/167–176
See application file for complete search history.

(56) References Cited

U.S. PATENT DOCUMENTS

| | | | | |
|---|---|---|---|---|
| 4,722,688 | A * | 2/1988 | Lonca | A61C 3/02 433/173 |
| 5,030,094 | A * | 7/1991 | Nardi | A61C 13/30 433/169 |
| 5,520,540 | A * | 5/1996 | Nardi | A61C 13/2656 433/172 |
| 5,788,493 | A | 8/1998 | Tanaka et al. | |
| 5,954,506 | A * | 9/1999 | Tanaka | A61C 8/0081 433/189 |
| 2002/0137010 | A1 * | 9/2002 | Honkura | A61C 8/0081 433/189 |
| 2003/0124491 | A1 * | 7/2003 | Honkura | A61C 8/0018 433/189 |
| 2006/0160048 | A1 * | 7/2006 | Honkura | A61C 13/235 433/189 |
| 2006/0216672 | A1 * | 9/2006 | Dinkelacker | A61C 8/0018 433/173 |
| 2006/0269903 | A1 * | 11/2006 | Bulard | A61C 8/005 433/174 |
| 2009/0117520 | A1 | 5/2009 | Kikuchi | |
| 2009/0220913 | A1 | 9/2009 | Geis-Gerstorfer et al. | |
| 2010/0055645 | A1 | 3/2010 | Mullaly et al. | |
| 2010/0190135 | A1 * | 7/2010 | Kalman | A61C 8/005 433/172 |
| 2010/0311014 | A1 | 12/2010 | Garcia Saban et al. | |
| 2012/0237900 | A1 * | 9/2012 | Lancieux | A61C 8/0022 433/174 |

FOREIGN PATENT DOCUMENTS

| | | |
|---|---|---|
| CN | 102131476 A | 7/2011 |
| JP | 7 136190 | 5/1995 |
| JP | 2007-75532 A | 3/2007 |
| JP | 2008-93126 A | 4/2008 |
| JP | 2009 131620 | 6/2009 |
| JP | 2011 504779 | 2/2011 |
| JP | 2012 501217 | 1/2012 |
| KR | 10-2012-0008672 A | 2/2012 |
| WO | 96 02206 | 2/1996 |
| WO | 2008 069086 | 6/2008 |

OTHER PUBLICATIONS

Combined Office Action and Search Report dated Oct. 23, 2015 in Chinese Patent Application No. 201380040590.4 (with English language translation and English Translation of Category of Cited Documents).
Taiwan Notification of Reasons for Refusal dated Jan. 18, 2016 in Taiwan Application No. 102124192, with English translation (8 pages).
Extended European Search Report dated Mar. 17, 2016, issued in Application No. EP 13 82 6141, 8 pages.
Second Office Action dated Jun. 23, 2016 in Chinese Patent Application No. 201380040590.4 (with English language translation).
Chinese Office Action for CN201380040590.4, dated Mar. 9, 2017. English translation provided.
Chines Office Action dated Sep. 12, 2017, for Chinese Patent Application 201380040590.4. (English translation provided).

* cited by examiner

S ←→ N

S ←→ N

IMPLANT OVERDENTURE SYSTEM AND IMPLANT

TECHNICAL FIELD

The invention relates to an implant overdenture system for fixing an implant overdenture onto alveolar ridge by the support of the dental implants and to dental implants used in the system.

BACKGROUND ART

In the field of dentistry, a technique called "implant overdenture system" for stabilizing an implant overdenture fixed in oral cavity is known. The implant overdenture system provides a structure in which the implant overdenture is fixed onto alveolar ridge by the support of dental implants configured to be inserted in alveolar ridge.

An implant has an implant body configured to be inserted in alveolar ridge, and an implant-side connector attached to an end of the implant body and configured to be exposed to oral cavity.

The implant overdenture is furnished with a plurality of artificial teeth, and a denture base for the plurality of artificial teeth to be fixed thereto. The denture base is structured to cover the alveolar ridge. The implant overdenture further has a denture-side connector in the denture base, and this connector is coupled to the implant-side connector.

As described later, magnetism-mediated coupling and mechanical coupling have so far been disclosed as means for coupling the denture-side and implant-side connectors.

Under the standards set forth in the Pharmaceutical Affairs Law, the implants conventionally used in the implant overdenture systems are generally divided into following types: relatively large implants having a body diameter of 3.0 mm or more and 7 mm or less and generally known as implant, and smaller implants having a body diameter of less than 3.0 mm and generally called "mini-implant".

Patent Document 1 discloses a technique using the relatively large implants wherein the implant overdenture is fixed to these implants by a magnetic force. The implant-side connector includes a keeper formed from a magnetic material, and the denture-side connector includes a magnetic assembly inserted in the denture base. The implant overdenture is fixed to the implants by making the keeper be attracted to the magnetic assembly by its magnetic force.

Some known implant overdenture systems using the mini-implants are structured to mechanically fix the implant overdenture to the mini-implants. The implant-side connector has a substantially cylindrical shape. The implant-side connector has a head part formed on an edge side thereof, and a fallen groove formed in the border between the head part and the implant body. The denture-side connect or has a cavity including a housing that can accommodate therein the head part, and an O ring provided between the fallen groove and the housing. The head part is located in the housing, and the implant overdenture is then fixed to the mini-implants by a fastening force generated by the O ring.

PRIOR ART DOCUMENT

Patent Document

Patent Document 1: JP-A-H07-136190

SUMMARY OF THE INVENTION

Problems to be Solved by the Invention

The implant overdenture system disclosed in Patent Document 1 has following problems.

The implant overdenture system disclosed in Patent Document 1 uses the magnetic force to fix the implant overdenture to the implants. This provides an advantage that the implant overdenture is readily attachable and detachable. On the other hand, it is necessary to save an enough area for attraction between the keeper and the magnetic assembly to exert a magnetic attractive force large enough to fix the implant overdenture. The implant overdenture system, therefore, demands the use of relatively large implants conventionally available.

The conventional implants may require about three surgical procedures, including inserting the implant in alveolar ridge before the implant overdenture system is ready to be used. More specifically, the first procedure involves drilling in jawbone and planting implants, and the second procedure involves incision into gingiva (punching) and formation of holes in gingiva. The third procedure is for placement of a prepared prosthesis, implant overdenture, on the implants. These procedures take an extensive period of time of approximately six months, often resulting in high surgical expenses (in this description, the surgical procedures associated with conventional implants are hereinafter simply called "conventional procedures").

In contrast, the implant overdenture system that mechanically fixes the implant overdenture to the mini-implants can significantly reduce the number of surgical procedures to be performed, duration of the whole process, and costs as compared to the conventional implants. More specifically, jawbone drilling and gingiva incision, planting the implants, and placement of the implant overdenture are all completed in one surgical procedure (in this description, the surgical procedure associated with the mini-implant is hereinafter called "mini-implant procedure").

The mini-implants diametrically smaller than the conventional implants are, however, difficult to use in the magnetism-mediated structure of Patent Document 1. Due to the fact, this document discloses the use of a mechanical fixing structure. The mechanical fixing structure has difficulty in attachability/detachability as compared to the magnetism-mediated structure. This raises a maintainability problem.

The diametrically smaller mini-implants are inferior to the conventional implants in strength. A force, if laterally applied to the mini-implant in a direction intersecting with an axial direction, imposes a rotation moment on the mini-implant. A description is given below of the structure of jawbone in which the mini-implant is configured to be inserted and mechanism of the rotation moment applied to the mini-implant inserted in jawbone.

Jawbone of alveolar ridge in which the mini-implant is configured to be inserted includes compact bone formed on a surface of jawbone, and cancellous bone formed inside of the compact bone.

The compact bone is approximately 1 mm in thickness from the surface of jawbone and has compact and hard osseous tissues. The cancellous bone has porous and soft osseous tissues in contrast to the compact bone.

When a force is laterally applied to the mini-implant fixed in jawbone, vicinity of sites held by the compact bone functions as fulcrum, and a rotation moment is generated in the mini-implant. At the time, the cancellous bone, though softer than the compact bone, generates a counterforce against the rotation of the mini-implant. The mini-implant undergoing the rotation moment and the resulting counterforce applied thereto is subject to a stress. This stress may deform the mini-implant, requiring repair and/or reconditioning.

The present invention was accomplished in view of these backgrounds. The present invention provides an implant overdenture system that involves less surgical burden, is readily attachable and detachable, and offers good maintainability; and an implant that can be used in the implant overdenture system and advantageously prevented from weakening in strength.

Solutions to the Problems

A first aspect of the present invention resides in an implant overdenture system for fixing an implant overdenture onto alveolar ridge by the support of implants, wherein
the implant overdenture including:
a plurality of artificial teeth;
a denture base for the plurality of artificial teeth to be fixed thereto, the denture base being structured to cover the alveolar ridge; and
a plurality of magnetic assemblies provided in the denture base,
the implants each including:
an implant body formed from a non-magnetic material and configured to be inserted in the alveolar ridge; and
a keeper formed from a magnetic material and provided at one end of the implant body so as to expose from the alveolar ridge,
the keeper and the magnetic assembly constituting a magnetic circuit, wherein:
a largest circumscribed circle diameter $d_1$ in an outer shape of a surface-to-be-attracted of the keeper attracted by the magnetic assembly is equal to or larger than $\varphi 1.8$ mm;
a largest diameter $d_2$ of the implant body is equal to or larger than $\varphi 1.2$ mm and equal to or less than $\varphi 3.5$ mm; and
the largest diameter $d_1$ and the largest diameter $d_2$ have a relationship expressed by $d_1/d_2 \leq 1.5$.

A second aspect of the present invention resides in an implant for fixing an implant overdenture onto alveolar ridge, including:
an implant body formed from a non-magnetic material and configured to be inserted in the alveolar ridge; and
a keeper formed from a magnetic material and configured to be exposed from the alveolar ridge,
the keeper and a magnetic assembly provided in the implant overdenture constituting a magnetic circuit,
the implant body including:
a threaded portion configured to be inserted in the alveolar ridge; and
an insert portion configured to be protruded from a base end of the threaded portion,
the keeper having a fallen insert portion that can accept therein the insert portion, wherein
a largest diameter $d_2$ of the implant body is equal to or larger than $\varphi 1.2$ mm and equal to or less than $\varphi 3.5$ mm, and the insert portion is inserted in the fallen insert portion to fix the implant body and the keeper to each other.

Effects of the Invention

Conventionally, the mini-implants are easy to process because the largest diameters of their implant bodies are rather small. On the contrary, using such mini-implants in any structure that leverages a magnetic force for fixing the implant overdenture may fail to obtain a magnetic attractive force large enough to fixedly stabilize the implant overdenture. A possible option to obtain a larger magnetic attractive force is to increase the outer shape of the surface-to-be-attracted of the keeper.

To enlarge the outer shape of the keeper in order to increase the magnetic attractive force between the magnetic assemblies and the keeper, however, results in offset of an outer peripheral portion of the keeper to a position more outward than an outer peripheral edge of the implant body. Any force applied to the offset portion in a direction intersecting with the surface-to-be-attracted generates a rotation moment, a point of support of which is vicinity of the sites held by compact bone.

The larger the offset of the surface-to-be-attracted is, the larger the rotation moment is. Thus, there is a possibility that a required strength of the implant may not be secured by simply enlarging the keeper. This was considered that commercializing a magnetism-mediated implant overdenture system for use with the mini-implants was difficult.

According to the first aspect, the largest circumscribed circle diameter $d_1$ in the outer shape of the surface-to-be-attracted of the keeper is equal to or larger than $\varphi 1.8$ mm, and the largest diameter $d_2$ of the implant body is equal to or larger than $\varphi 1.2$ mm and equal to or less than $\varphi 3.5$ mm, wherein the largest diameter $d_1$ and the largest diameter $d_2$ have a relationship expressed by $d_1/d_2 \leq 1.5$. Diametrically enlarging the keeper within such a suitable range of dimensions relative to the implant body can attain increases of the magnetic force, as well as reductions of the offset of the outer peripheral edge of the keeper from the implant body. This enhances the magnetic attractive force between the keeper and the implant body, while concurrently securing a required strength of the implant.

The magnetism-mediated fixing of the implant overdenture and the implants is advantageous because any force laterally applied to the implant overdenture is alleviated by slippage occurring between the keepers and the magnetic assemblies. This prevents a large lateral force from being transmitted to the implants, consequently avoiding possible damage and/or deformation of the implants.

The largest diameter $d_2$ of the implant body is set to a value equal to or larger than $\varphi 1.2$ mm and equal to or less than $\varphi 3.5$ mm. The implant with the largest diameter $d_2$ equal to or larger than $\varphi 3.0$ mm and equal to or less than $\varphi 3.5$ mm, though categorized as the conventional implant according to the Pharmaceutical Affairs Law, can be planted in one surgical procedure as with the mini-implants.

The implant with the largest diameter $d_2$ equal to or larger than $\varphi 1.2$ mm and less than $\varphi 3.0$ mm is categorized as the mini-implant and is conventionally planted by one surgical procedure. The implant with the largest diameter $d_2$ within the range of values equal to or larger than $\varphi 1.2$ mm and equal to or less than $\varphi 3.5$ mm advantageously requires only one implant surgical procedure as with the mini-implant procedure. Thus, the number of surgical procedures to be performed, duration of the whole process, and costs can be reduced as compared to the conventional implants.

In the above-described implant overdenture system, by selecting an optimum number of implants for fixing the implant overdenture, the implant overdenture can be fixed in a stable manner by the support of the implants.

Providing the plural implants increases a magnetic force that may be insufficient with only one implant, offering a magnetic attractive force large enough to fix the implant overdenture.

Conventionally, fixing the implant overdenture to the mini-implants by a magnetic force was considered almost infeasible. This implant overdenture system, however, can successfully fix the implant overdenture to the implants through magnetism by optimizing the number, dimensions, and positions of the implants.

This aspect of the invention can successfully acquire advantages with the conventional mini-implants; less number of surgical procedures to be performed, shorter duration of the whole process, and cost reduction, and advantages with magnetism-mediated fixing of the implant overdenture to the implants; good attachability/detachability and resultant improvement of maintainability.

In the implant according to the second aspect of the invention, the insert portion of the implant body is inserted into the fallen insert portion of the keeper to fix the implant body and the keeper to each other. This structural feature effectively prevents the strength of the implant from deteriorating in contrast to any implant having the implant body of the same outer shape in which the fallen insert portion is formed.

In the case of providing the fallen insert portion in the implant body diametrically downsized as described earlier, the implant body mostly reduces in thickness, often degrading in strength.

On the other hand, the keeper configured to be exposed from the alveolar ridge is unlikely to adversely affect the surgical procedure performed to insert the implant. Considering the magnetic attractive force between the magnetic assembly and the keeper, the keeper having an axially larger outer diameter is more advantageous. The outer shape of the keeper when axially viewed can optionally be increased to larger dimensions than the outer shape of the implant body to such an extent that strengths of the keeper and the implant body are well-balanced to each other. Therefore, the keeper with the fallen insert portion formed therein can still save an enough thickness.

Providing the fallen insert portion in the keeper can avoid deteriorating the strength of the implant body securing a required strength of the keeper, thereby preventing the whole implant from deteriorating in strength.

The largest diameter d2 of the implant body is set to a value equal to or larger than $\varphi 1.2$ mm and equal to or less than $\varphi 3.5$ mm. The implant with the largest diameter d2 equal to or larger than $\varphi 3.0$ mm and equal to or less than $\varphi 3.5$ mm, though categorized as the conventional implant according to the Pharmaceutical Affairs Law, can be planted in one surgical procedure as with the mini-implants.

The implant with the largest diameter d2 equal to or larger than $\varphi 1.2$ mm and less than $\varphi 3.0$ mm is categorized as the mini-implant and is conventionally planted in one surgical procedure. The implant with the largest diameter d2 within the range of values equal to or larger than $\varphi 1.2$ mm and equal to or less than $\varphi 3.5$ mm advantageously requires only one surgical procedure as with the mini-implant procedure. Thus, the number of surgical procedures to be performed, duration of the whole process, and costs can be reduced as compared to the conventional implants.

Due to this structure, it is possible to achieve advantages same as those of the conventional mini-implants, that is, less number of surgical procedures to be performed, shorter duration of the whole process, and cost reduction, and also possible to ensure strength that the conventional mini-implants cannot provide.

As described so far, the invention provides an implant overdenture system that involves less surgical burden, is readily attachable and detachable, and offers better maintainability; and a dental implant that can be used in the implant overdenture system and advantageously prevented from weakening in strength.

EMBODIMENTS OF THE INVENTION

Figure 1:
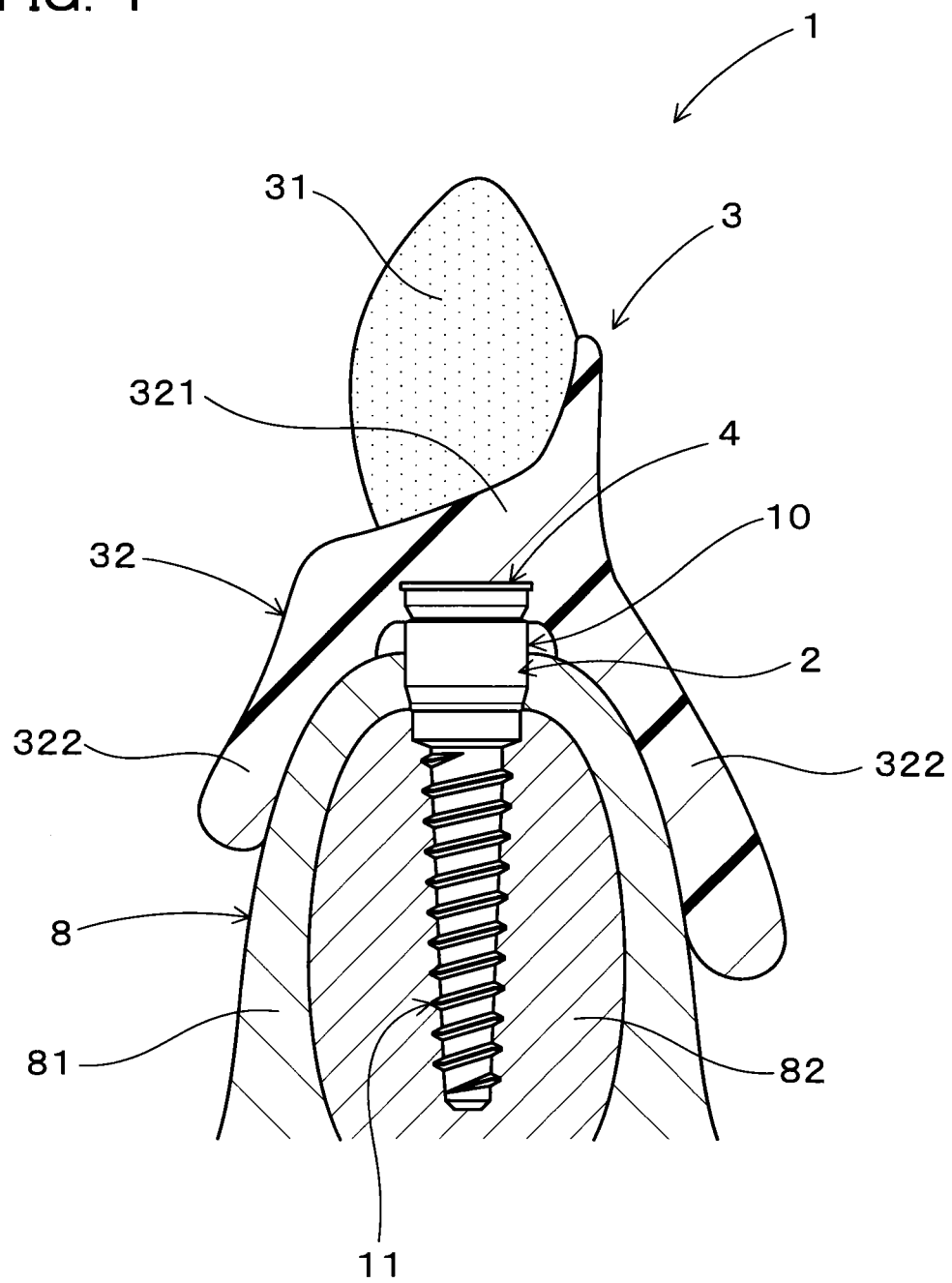
FIG. 1 is a drawing illustrating an implant overdenture system according to Example 1.

In the implant overdenture system, the largest circumscribed circle diameter d1 in the outer shape of the surface-to-be-attracted of the keeper is preferably equal to or larger than $\varphi 2.5$ mm. The largest diameter d1 is more preferably equal to or larger than $\varphi 3.0$ mm. These numeral ranges further ensure that a sufficient magnetic attractive force is exerted between the keeper and the magnetic assembly of the implant overdenture.

The largest diameter d1 less than φ1.8 mm may weaken the magnetic attractive force exerted between the keeper and the magnetic assembly.

The largest diameter d1 attributes to the largest diameter d2 of the implant body. The largest diameter d1 is, therefore, selected from values meeting a relationship expressed by d1/d2≤1.5. The values of d1/d2 greater than 1.5 increase the offset of the outer periphery of the keeper from the implant body. If a force is applied to the offset portion in a direction intersecting with the surface-to-be-attracted of the keeper, the implant body may undergo an excessive rotation moment generated by the force.

The largest diameters d1 and d2 preferably meet a relationship expressed by d1/d2≤1.3. The largest diameters d1 and d2 more preferably meet a relationship expressed by d1/d2≤1.2. The values of the largest diameters d1 and d2 meeting these relationships are best-balanced to each other.

In the implant overdenture system and the implant, the largest diameter d2 of the implant body is preferably equal to or larger than φ2.0 mm and equal to or less than φ3.3 mm. The largest diameter d2 is more preferably equal to or larger than φ2.5 mm and equal to or less than φ3.0 mm. These numeral ranges further ensure improvements in the strength of the implant and reductions of the number of surgical procedures to be performed, duration of the whole process, and costs.

The values of the largest diameter d2 less than φ1.2 mm may result in an insufficient strength of the implant body.

The values of the largest diameter d2 greater than φ3.5 mm involves the risk that the whole process associated with the implant overdenture system may not be completed in one surgical procedure.

The magnetic assemblies may be provided at bilaterally symmetrical positions in the implant overdenture. This structure helps an occlusal pressure applied to the implant overdenture to be evenly dispersed onto the alveolar ridge through the implant. The implant overdenture may be accordingly fixed in a stable manner onto the alveolar ridge.

The implant overdenture system described herein may use two to four pairs of implants and magnetic assemblies. This allows well-balanced layouts of the implants, while ensuring a magnetic attractive force large enough to fix the implant overdenture. The implant overdenture is accordingly fixed in a stable manner.

Less than two pairs of magnetic assemblies and implants may fail to attain an enough magnetic force to fix the implant overdenture, resulting in failure to have a sufficient magnetic attractive force.

More than four pairs of magnetic assemblies and implants may lead to prolonged surgical time and cost increase.

The implant overdenture may be structured to be contour to the alveolar ridge of mandible and to be fixable to the implants planted in the alveolar ridge of mandible. According to the structure in which the mandible supports the implant overdenture from therebelow, the implant overdenture is better supported and held than the maxilla. The implant overdenture thus specifically designed for mandible can be fixed in a more stable manner.

Preferably, the largest circumscribed circle diameter d1 in the outer shape of the surface-to-be-attracted of the keeper attracted by the magnetic assembly is equal to or larger than φ1.8 mm, and the largest diameters d1 and d2 have a relationship expressed by d1/d2≤1.5. The values of the largest diameters d1 and d2 meeting this relationship are well-balanced to each other. The largest diameters thus defined ensure that the magnetic attractive force between the magnetic assembly and the keeper is large enough, and also prevent the implant from undergoing an excessive rotation moment generated by any force applied to the surface-to-be-attracted of the keeper in a direction intersecting with the surface-to-be-attracted.

The largest diameters d1 and d2 preferably meet a relationship expressed by d1/d2≤1.3. The largest diameters d1 and d2 more preferably meet a relationship expressed by d1/d2≤1.2. The values of the largest diameters d1 and d2 meeting these relationships are best-balanced to each other.

The implant may be structured to fix the implant body and the keeper to each other by press-fitting the insert portion into the fallen insert portion. In this case, the implant body and the keeper can be readily and efficiently fixed to each other. This leads to an improved productivity.

Optionally, the insert portion has an external thread portion with threads formed on an outer peripheral side surface thereof, and the fallen insert portion has an internal thread portion with threads formed on an inner peripheral side surface thereof. The implant body and the keeper may be fixed by engaging the external and internal thread portions with each other. In this case, the keeper can be easily removed from the implant body. This further improves the maintainability of the implant. The keeper, which is a magnetic member, is usually projected as a shadowed part on images such as MRI images. The keeper thus conveniently removable is prevented from appearing on such images.

The keeper may have a titanium nitride film formed on at least an outer peripheral side surface thereof. In case of a patient who may be allergic to the metallic material of the keeper, this film may prevent the keeper from contacting a patient's gingiva, avoiding occurrence of his/her allergic symptoms.

EXAMPLES

Example 1

Examples of the implant overdenture system and implant used in the same are hereinafter described referring to FIGS. 1 to 6.

As illustrated in FIG. 1, an implant overdenture system 1 is used to fix an implant overdenture 3 onto alveolar ridge 8 by the support of dental implants 10.

The implant overdenture 3 has a plurality of artificial teeth 31, a denture base 32 for the plurality of artificial teeth 31 to be fixed thereto. The denture base 32 is structured to cover gingiva 81 of the alveolar ridge 8. The implant overdenture 3 further has a plurality of magnetic assemblies 4 provided in the denture base 32.

Figure 2:
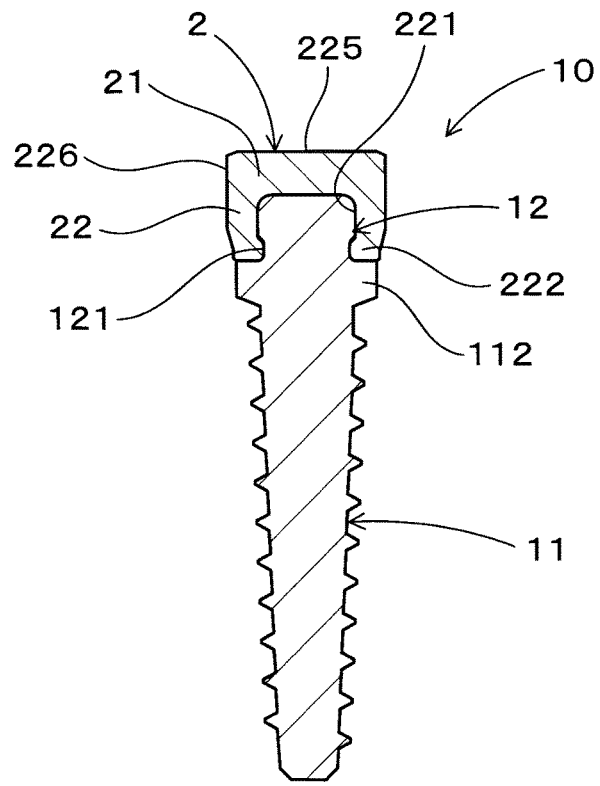
FIG. 2 is a sectional view of an implant according to Example 1.

As illustrated in FIG. 2, the implant 10 includes an implant body 11 formed from a non-magnetic material and configured to be inserted in the alveolar ridge 8, and a keeper 2 formed from a magnetic material and provided at one end of the implant body 11 so as to expose from the alveolar ridge 8. The keeper 2 and the magnetic assembly 4 constitute a magnetic circuit.

Figure 3:
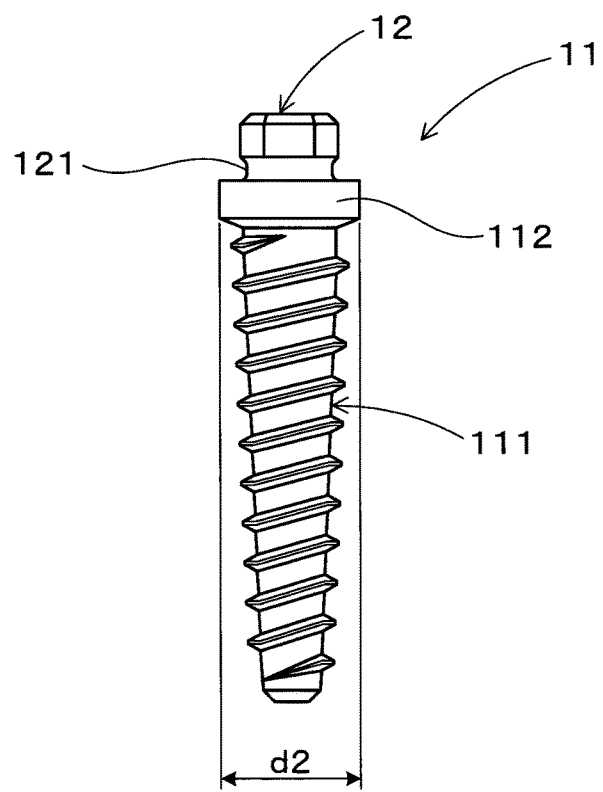
FIG. 3 is an external view of an implant body according to Example 1.
Figure 4A:
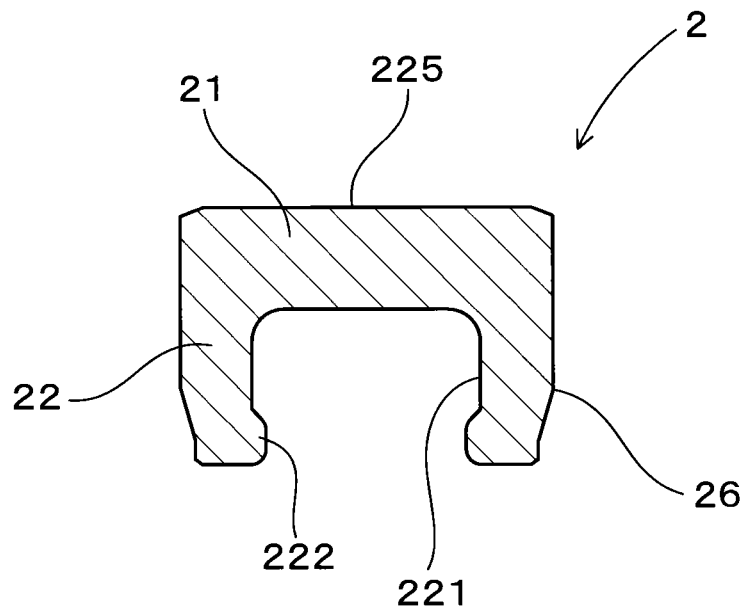
FIG. 4(a) is a sectional view illustrating the structure of a keeper.
Figure 4B:
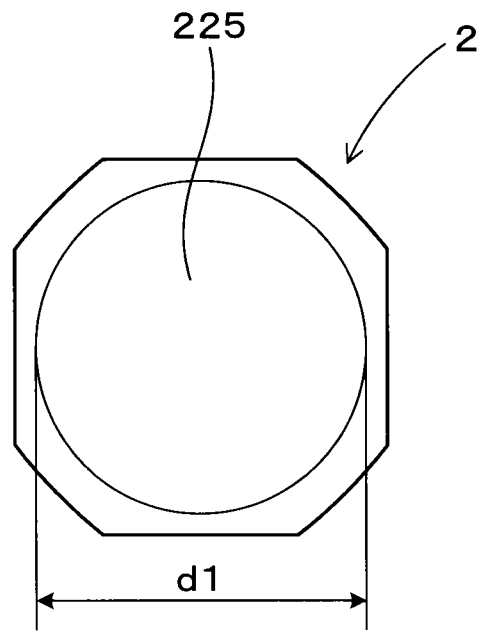
FIG. 4(b) is a top view of the keeper, according to Example 1.

As illustrated in FIGS. 3 and 4, a largest circumscribed circle diameter d1 in an outer shape of a surface-to-be-attracted 225 of the keeper 2 attracted by the magnetic assembly 4 is φ3.0 mm. A largest diameter d2 in an inserted part of the implant body 11 is φ2.5 mm. Hence, the largest diameters d1 and d2 have a relationship expressed by d1/d2≤1.5.

A further detailed description is hereinafter given.

Figure 6:
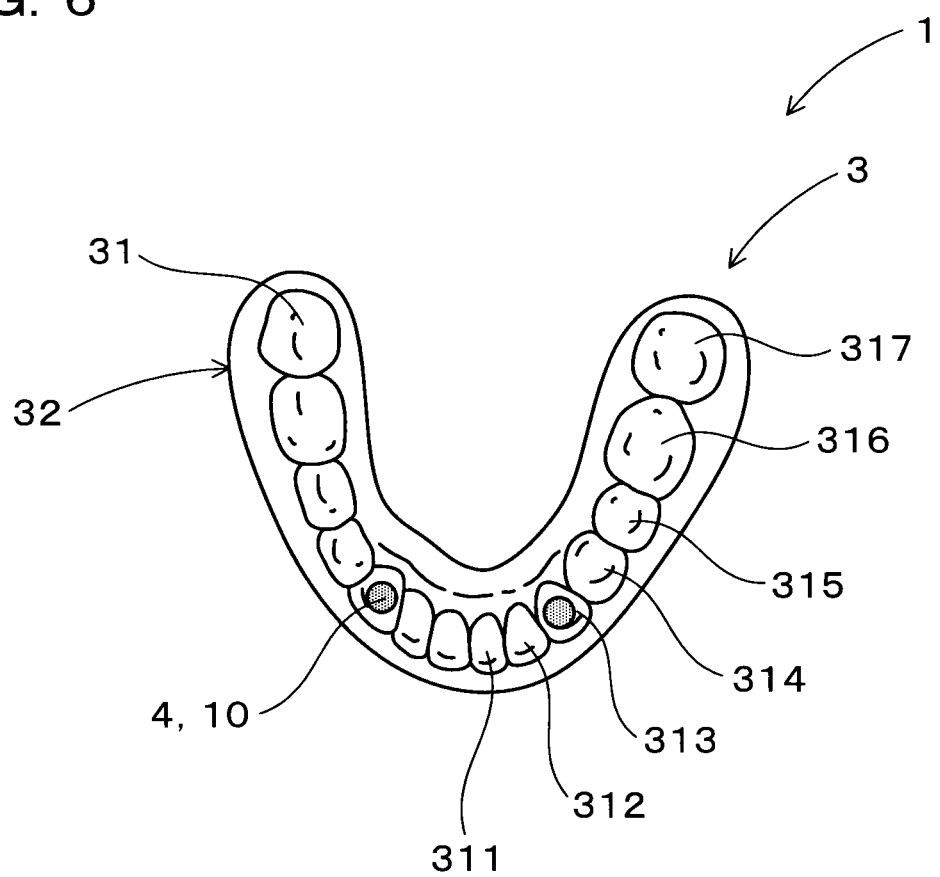
FIG. 6 is a top view of the implant overdenture system according to Example 1.

As illustrated in FIGS. 1 and 6, the implant overdenture system 1 of this example is furnished with two implants 10 configured to be inserted in the alveolar ridge 8, and the implant overdenture 3 fixed to the implants 10.

As illustrated in FIG. 1, the alveolar ridge 8 of edentulous mandible includes the gingiva 81 formed on the surface of the alveolar ridge, and jawbone 82 covered with the gingiva 81. The alveolar ridge 8 is substantially U-shaped in view from upward and substantially mountain-shaped in cross section.

The implant overdenture 3 is placed so as to cover the alveolar ridge 8. The implant overdenture 3 includes the plurality of artificial teeth 31, the denture base 32 for the artificial teeth 31 to be fixed thereto, and the magnetic assemblies 4. The keeper 2 of the implant 10 and the magnetic assembly 4 constitute a magnetic circuit.

As illustrated in FIGS. 1 and 6, the denture base 32 is substantially U-shaped in view from upward. The denture base 32, referring to its shape in cross section, includes a summit portion 321 provided at an upper part thereof, and a side wall portion 322 obliquely extending downward from two lateral sides of the summit portion 321. The denture base 32 has a mountain-like shape in cross section and has an opening formed on its lower side. The inner surface of the denture base 32 is formed by taking a cast of the alveolar ridge 8, therefore, has a shape contour to the alveolar ridge 8.

As illustrated in FIG. 6, the plurality of artificial teeth 31 provided in the denture base 32 respectively have shapes coincident with those of central incisors 311, lateral incisors 312, canines 313, first premolars 314, second premolars 315, first molars 316, and second molars 317. Of the artificial teeth 31, two each are located at substantially bilaterally symmetrical positions on the upper surface of the summit portion 321 of the denture base 32. There are 14 artificial teeth 31 in total in one denture base 32.

Figure 5A:
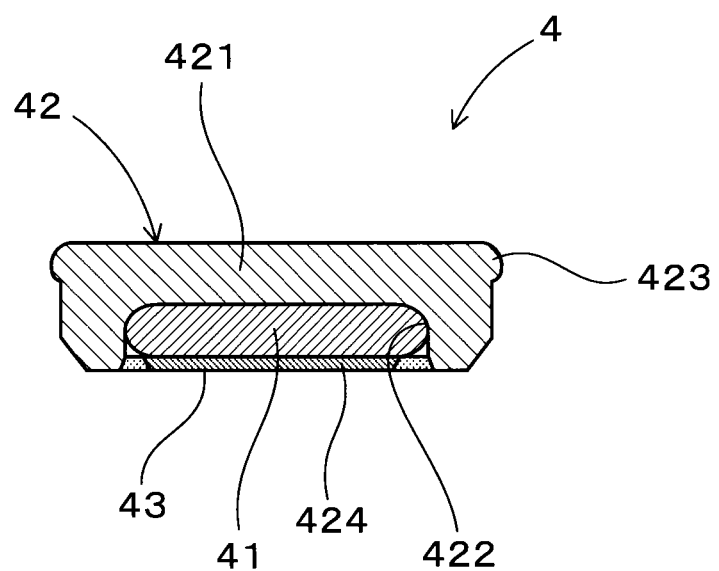
FIG. 5(a) is a sectional view illustrating the structure of a magnetic assembly, and FIG. 5 (b) is a bottom view of the magnetic assembly, according to Example 1.
Figure 5B:
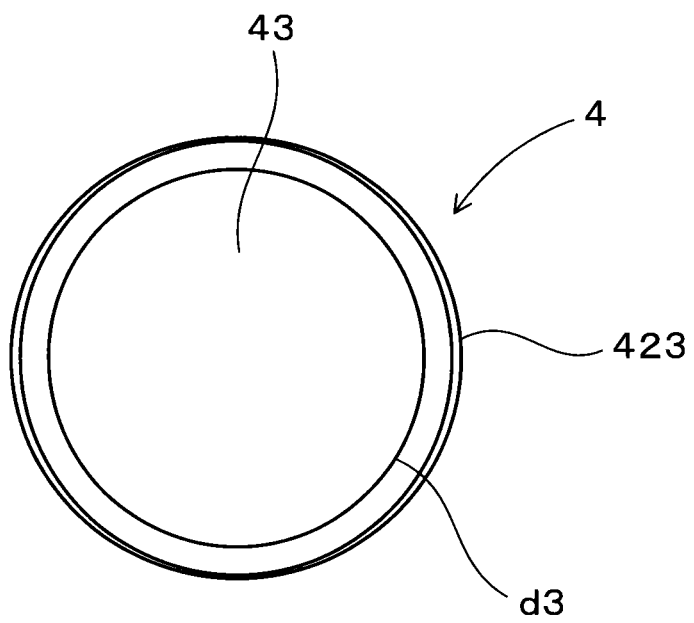

As illustrated in FIGS. 1 and 5, the magnetic assembly 4 provided in the denture base 32 has a substantially disc shape, and includes a permanent magnet 41 and a yoke 42 covering the magnet 41.

The permanent magnet 41 of the magnetic assembly 4 is substantially disc-shaped, and the whole circumference of this magnet is covered with the yoke 42. The yoke 42 is formed from a soft magnetic stainless steel. The yoke 42 includes a yoke body 421 having a fallen locating portion 422 with an opening formed on its lower side, and a lid 424 covering the opening of the fallen locating portion 422. The yoke body 421 has a flange 423 extending from an upper end toward an outer peripheral side thereof. The flange 423 has an elliptical shape when vertically viewed. When the magnetic assembly 4 is inserted in the denture base 32, the flange 423 serves to prevent the magnetic assembly from falling out or rotating. Describing the structure of the yoke 42, the permanent magnet 41 is provided in the fallen locating portion 422 of the yoke body 421, and the opening of the yoke 42 is sealed with the lid 424, so that the permanent magnet 41 is enclosed therein.

As illustrated in FIGS. 1 and 5, the lower surface of the magnetic assembly 4 constitutes an attractive surface 43 that is circular, smooth and flat. A largest circumscribed circle d3 of the attractive surface 43 is φ3.0 mm in diameter. On the back surface of the summit portion 321 of the denture base 32, the magnetic assemblies 4 are inserted, with their attractive surfaces 43 alone being exposed, at positions located correspondingly to the two implants 10 planted in the alveolar ridge 8.

As illustrated in FIGS. 1 and 2, the implant 10 for fixing the denture base 32 onto the alveolar ridge 8 includes the implant body 11 formed from a non-magnetic material and configured to be inserted in the alveolar ridge 8, and the keeper 2 provided at an upper end of the implant body 11.

As illustrated in FIGS. 2 and 3, the implant body 11, the material of which is a titanium alloy, includes a threaded portion 111 with threads formed on an outer peripheral side surface thereof, a flange 112 extending from a base end of the threaded portion 111 toward the outer peripheral side, and an insert portion 12 protruding above the upper surface of the flange 112.

As illustrated in FIG. 3, the threaded portion 111 has a spiral thread axially formed on the outer peripheral side surface. The threaded portion 111 is formed in a tapered shape having an outer diameter progressively smaller toward its edge.

The insert portion 12 standing upward from the upper surface of the flange 112 has a polygonal columnar shape forming a hexagonal shape when axially viewed. The insert portion 12 has a diametrically smaller fallen groove 121 formed on the border with the flange 112. In this example, the largest diameter d2 of the implant body 11 is φ2.5 mm.

As illustrated in FIG. 4, the keeper 2 mounted on the insert portion 12 is formed from a soft magnetic stainless steel. The keeper 2 has a substantially tetragonal shape, when viewed from upward, defined by four sides and four arcs connecting the four sides. The keeper 12 includes a keeper upper surface portion 21 having a plate-like shape, and a keeper side wall portion 22 having a substantially cylindrical shape and extending downward from an outer peripheral edge of the keeper upper surface portion 21.

The keeper upper surface portion 21 has a smooth and flat surface-to-be-attracted 225 having a circular shape when viewed from upward. On an outer peripheral side of the keeper upper surface portion 21 than the surface-to-be-attracted 225, there is a tapered surface progressively inclined downward as more distant from the surface 225.

The attractive surface 43 of the magnetic assembly 4 and the surface-to-be-attracted 22 of the keeper 2 are both flat surfaces. The magnetic assembly 4 and the keeper 2 are accordingly tightly fitted to each other. This minimizes an air gap in the magnetic circuit, promising a sufficient magnetic attractive force.

Similarly to the attractive surface 43 of the magnetic assembly 4, a largest circumscribed circle diameter d1 of the surface-to-be-attracted 225 is φ3.0 mm. Hence, the largest circumscribed circle diameter d1 of the surface-to-be-attracted 225 and the largest diameter d2 of the implant body meet a relationship expressed by d1/d2=1.2.

In this example, the surface-to-be-attracted 225 and the attractive surface 43 have an identical shape. However, these surfaces may differ in shape and dimension.

As illustrated in FIGS. 2 and 4, the inner periphery of the keeper side wall portion 22 constitutes a fallen insert portion 221 formed correspondingly to the insert portion 12. The fallen insert portion 221 has an inner peripheral surface substantially hexagonal when axially viewed. An inner peripheral flange 222 extending inward is formed at an opening end of the fallen insert portion 221. The inner peripheral flange 222 is engageable with the fallen groove 121 of the insert portion 12. A titanium nitride film is formed on an outer peripheral side surface 226 of the keeper side wall portion 22.

As illustrated in FIG. 2, the implant body 11 and the keeper 2 constitute the implant 10. The implant body 11 and the keeper 2 are fixed to each other by press-fitting the insert portion 12 into the fallen insert portion 221.

As illustrated in FIG. 6, the implants 10 are planted at positions in the alveolar ridge 8 which are located correspondingly to the artificial teeth 31 of the implant overdenture 3 as replacements for a pair of canines 313. The implants 10 are respectively planted at substantially bilaterally symmetrical positions in the alveolar ridge 8. Any positions that are roughly linearly symmetrical to the median line may be defined as bilaterally symmetrical positions. When the attractive surfaces 43 of the magnetic assemblies 4 provided in the implant overdenture 3 attract to the surfaces-to-be-attracted 225 of the keepers 2 in the implants 10, the implant overdenture 3 is securely fixed onto the alveolar ridge 8.

The effects of this example are described below.

According to the implant overdenture system 1 of this example, the largest circumscribed circle diameter d1 in the outer shape of the surface-to-be-attracted 225 of the keeper 2 is φ3.0 mm, and the largest diameter d2 of the implant body 11 is φ2.5 mm. The largest diameter d1 and the largest diameter d2 have a relationship expressed by d1/d2=1.2. Diametrically enlarging the keeper 2 within a suitable range of dimensions attains increases of the magnetic force, as well as reductions of offset of the outer peripheral edge of the keeper 2 from the implant body 11. This enhances the magnetic attractive force between the keeper 2 and the implant body 11, while concurrently securing a required strength of the implant 10.

The magnetism-mediated fixing of the implant overdenture 3 and the implants 10 is advantageous because any force laterally applied to the implant overdenture 3 is alleviated by slippage occurring between the keepers 2 and the magnetic assemblies 4. This prevents a large lateral force from being transmitted to the implants 10, consequently avoiding possible damage and/or deformation of the implants 10.

When the largest diameter d2 of the implant body 11 is decided as described earlier, planting the implant 10 is completed in one surgical procedure similarly to the mini-implant method instead of several procedures conventionally required. Thus, a number of surgical procedures to be performed, duration of the whole process, and costs are all advantageously reduced as compared to the conventional implants.

In the implant overdenture system described herein, by selecting an optimum number of implants 10 for fixing the implant overdenture 3, the implant overdenture 3 can be fixed in a stable manner by the support of the implants 10.

Providing two implants 10 allows the implants to be arranged in a well-balanced manner, while ensuring a magnetic attractive force large enough to fix the implant overdenture 3. The implant overdenture 3 is accordingly fixed in a stable manner.

Conventionally, fixing the implant overdenture 3 to the mini-implants by a magnetic force was considered almost infeasible. The implant overdenture system 1, however, can successfully fix the implant overdenture 3 to the implants 10 through magnetism by optimizing the number, dimensions, and positions of the implants 10 to be planted.

Due to this structure, it is possible to achieve advantages same as those of the conventional mini-implants, that is, less number of surgical procedures to be performed, shorter duration of the whole process, and cost reduction; and also possible to achieve advantages with magnetism-mediated fixing of the implant overdenture to the implants, that is, good attachability/detachability and resultant improvement of maintainability.

The magnetic assemblies 4 are situated at bilaterally symmetrical positions in the implant overdenture 3. This structure helps an occlusal pressure applied to the implant overdenture 3 to be evenly dispersed onto the alveolar ridge 8 through the implants 10. The implant overdenture 3 may be accordingly fixed in a stable manner onto the alveolar ridge 8.

The implant overdenture 3 is structured to contour to the alveolar ridge 8 of mandible and to be fixable to the implants 10 planted in the alveolar ridge 8 of mandible. According to the structure in which the mandible supports the implant overdenture 3 from therebelow, the implant overdenture 3 is better supported and held than the maxilla. The implant overdenture 3 thus specifically designed for mandible can be fixed in a more stable manner.

In the implant 10, the insert portion 12 of the implant body 11 is inserted into the fallen insert portion 221 of the keeper 2 to fix the implant body 11 and the keeper 2 to each other. This structural feature effectively prevents the strength of the implant 10 from weakening in contrast to any implant having the implant body 11 of the same outer shape in which the fallen insert portion 221 is formed.

In the case of providing the fallen insert portion 221 in the implant body 11 diametrically downsized as described earlier, the implant body 11 mostly reduces in thickness, often degrading in strength.

On the other hand, the keeper 2 configured to be exposed from the alveolar ridge 8 is unlikely to adversely affect the surgical procedure performed to insert the implant 10. Considering the magnetic attractive force between the magnetic assembly 4 and the keeper 2, the keeper 2 having an axially larger outer diameter is more advantageous. The outer shape of the keeper 2 when axially viewed can optionally be increased to larger dimensions than the outer shape of the implant body 11 to such an extent that strengths of the keeper 2 and the implant body 11 are well-balanced to each other. The keeper 2 with the fallen insert portion 221 formed therein can still save an enough thickness.

Providing the fallen insert portion 221 in the keeper 2 can avoid weakening of the implant body 11 while ensuring a required strength of the keeper 2, thereby preventing the whole implant 10 from deteriorating in strength.

The implant 10 is structured to fix the implant body 11 and the keeper 2 to each other by press-fitting the insert portion 12 into the fallen insert portion 221. According to the structure, the implant body 11 and the keeper 2 can be readily and efficiently fixed to each other. This leads to an improved productivity.

The keeper 2 has a titanium nitride film formed on at least an outer peripheral side surface thereof. In the case of a patient who may be allergic to the metallic material of the keeper 2, this film prevents the keeper 2 from contacting the patient's gingiva, avoiding occurrence of his/her allergic symptoms.

The implant 10 of this example is screwed into a prepared hole formed in the alveolar ridge 8 after the implant body 11 and the keeper 2 are fixed to each other by press-fitting. The insert portion 12 of the implant body 11 has a polygonal columnar shape forming a hexagonal shape when axially viewed. This particular shape certainly promises integral rotation between the implant body 11 and the keeper 2 when the implant 10 is screwed into the prepared hole, instead of relative rotation therebetween.

As described so far, this example provides the implant overdenture system 1 with less surgical burden that is readily attachable and detachable, offering better maintainability, and the implant 10 advantageously prevented from weakening in strength.

Example 2

This example presents modified shapes of the insert portion 12 and the fallen insert portion 221 of the implant 10 according to Example 1.

Figure 7A:
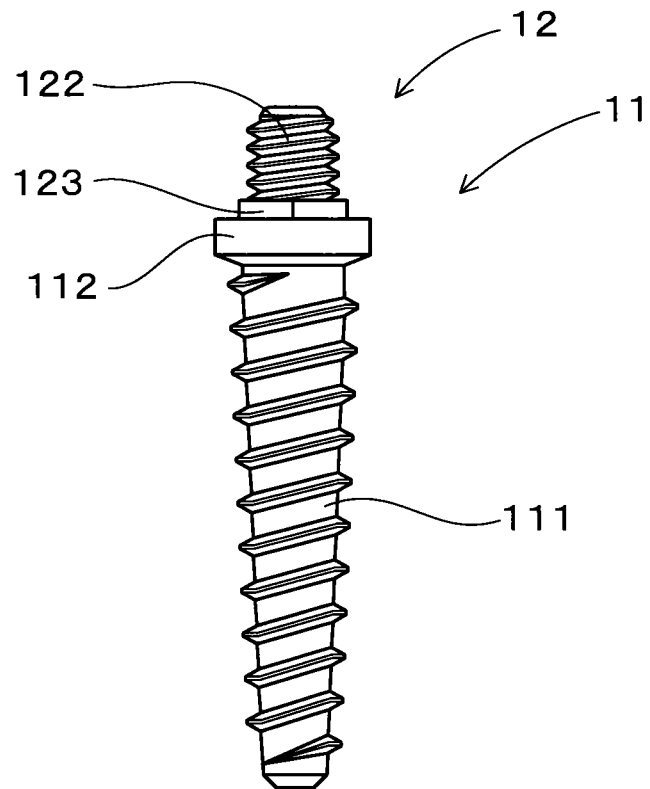
FIG. 7 (a) is an external view illustrating an implant body.
FIG. 7(b) is a sectional view of a keeper according to Example 2.
Figure 7B:
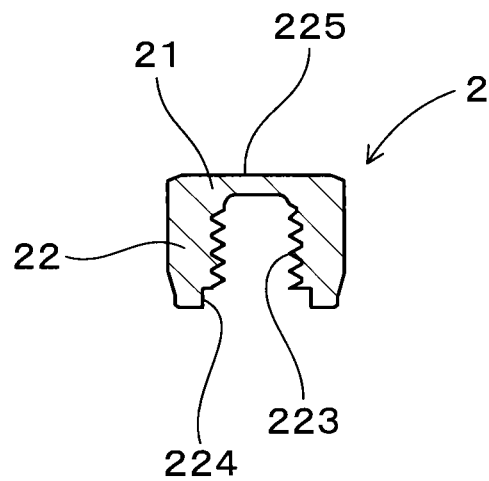

As illustrated in FIG. 7 (a), the insert portion 12 of the implant body 11 has a fastening-engaging portion 123 having a regular hexagonal shape when viewed from upward, and an external thread portion 122 formed on the upper surface of the fastening-engaging portion 123. The external thread portion 122 has a cylindrical shape with threads formed on an outer peripheral side surface thereof.

As illustrated in FIG. 7 (b), an internal thread portion 223 is formed correspondingly to the external thread portion 122 on the inner peripheral surface of the fallen insert portion 221 of the keeper 2. Provided at an opening end part of the fallen insert portion 221 is an enlarged opening 224 that can accept therein the fastening-engaging portion 123 of the insert portion 12.

To plant the implant 10 in the alveolar ridge 8 according this example, the implant body 11 is inserted in the alveolar ridge 8 by engaging a tool with the fastening-engaging portion 123. Then, the keeper 2 is engaged with the external thread portion 122 exposed from the alveolar ridge 8, so that the formation of the implant 10 is completed.

Any other technical features are similar to Example 1.

In the implant overdenture system 1 of this example, the insert portion 12 includes the external thread portion 122 with threads formed on its outer peripheral side surface, and the fallen insert portion 221 includes the internal thread portion 223 with threads formed on its inner peripheral side surface. The implant body 11 and the keeper 2 are fixed by engaging the external and internal thread portions 122 and 223 with each other. According to the structure, the keeper 2 can be easily removed from the implant body 11. This further improves the maintainability of the implant 10. The keeper 2, which is a magnetic member, is usually projected as a shadowed part on images such as MRI images. The keeper 2 thus conveniently removable is prevented from appearing on such images.

Example 3

This example presents a modified structure of the magnetic assembly 40 in the implant overdenture system 1 of Example 1.

Figure 8:
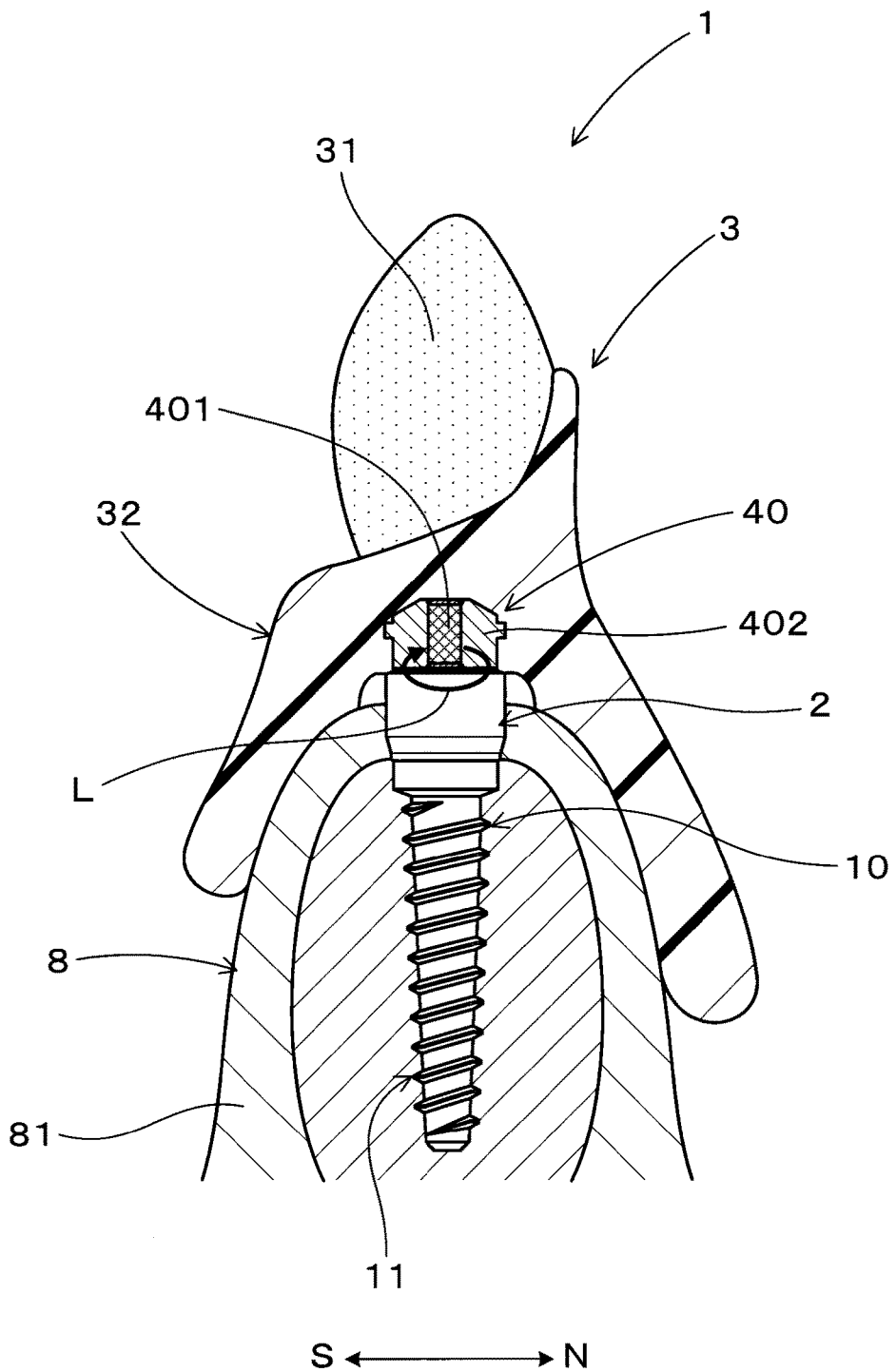
FIG. 8 is a sectional view of an implant overdenture system according to Example 3.
Figure 9A:
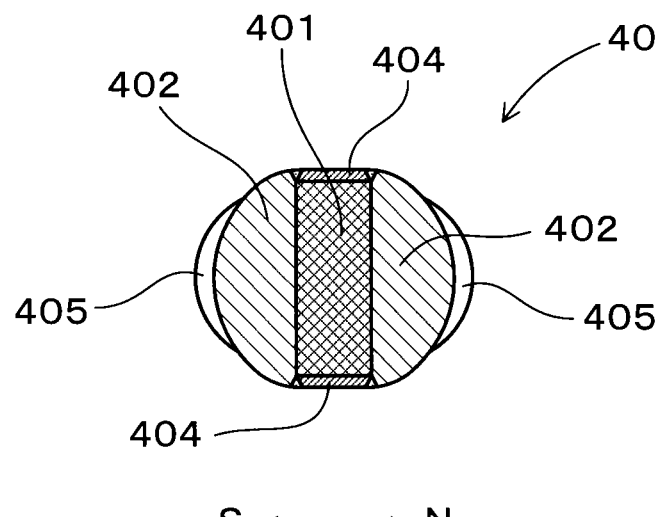
FIG. 9(a) is a sectional view illustrating the structure of a magnetic assembly taken along a plane.
Figure 9B:
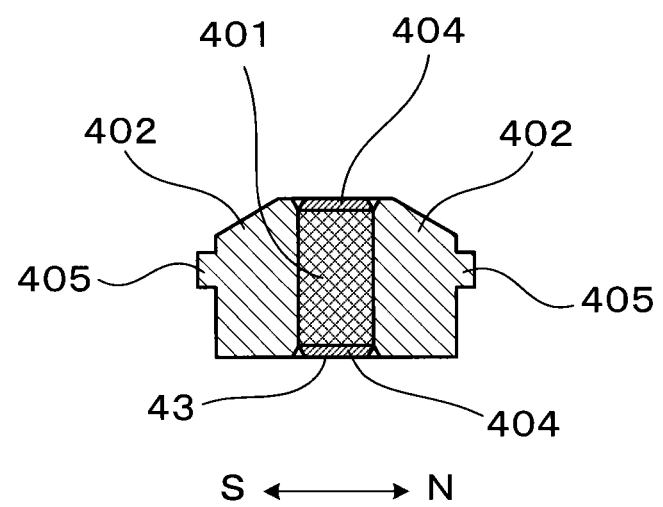
FIG. 9(b) is a sectional view illustrating the structure of the magnetic assembly taken along a vertical plane, according to Example 3.

As illustrated in FIGS. 8 and 9, this magnetic assembly 40 has a permanent magnet 401, a pair of yokes 402 provided on two lateral sides of the permanent magnet 401, and a shield case 404 that covers most of a surface of the permanent magnet 401 except parts of the surface where the pair of yokes 402 is provided.

As illustrated in FIG. 9, the permanent magnet 401 is magnetized so that a direction of magnetic poles (N (north) and S (south) poles) (a direction illustrated with an arrow in the drawing) is coincident with a direction where the pair of yokes 402 and the permanent magnet 401 are juxtaposed. The permanent magnet 401 is in the form of a hexagonal block when viewed in the direction of juxtaposition.

The shield case 404 is formed from a non-magnetic material and covers the surface of the permanent magnet 401 situated in a direction orthogonal to the direction of juxtaposition. This prevents the magnetism of the permanent magnet 401 from leaking in any direction but the direction of juxtaposition.

The pair of yokes 402 is formed from a soft magnetic stainless steel. The yokes 402, when viewed from the direction of juxtaposition, has a hexagonal shape coincident with the outer shape of the permanent magnet 401 shielded by the shield case 404. Viewing the yoke 402 from the top, its outer side surface opposite to the permanent magnet 401 has a circular arc shape. The outer side surface has a flange 405 extending outward so that the magnetic assembly 40 provided in the denture base 32 does not fall out.

Any other technical features are similar to Example 1.

When the keeper 2 is attracted to the magnetic assembly 40, the magnetic assembly 40 and the keeper 2 form a magnetic loop L circulated therebetween. This magnetic loop L is circulated from the N pole of the permanent magnet 401 through the pair of yokes 402 and the keeper 2 to the S pole of the permanent magnet 401. The magnetic loop L formed in this manner can generate an intense magnetic force, exerting a powerful magnetic attractive force. This favorably improves the magnetic attractive force in a limited attraction area, enabling the implant overdenture 3 to be more reliably fixed. The magnetic assembly 40 often increases in height as compared to conventional magnetic assemblies. Therefore, the magnetic assemblies 40 are preferably provided in a front-teeth part with more room in the height direction than the other parts.

This example can attain effects similar to Example 1.

Example 4

This example presents a modified structure of the implant overdenture system 1.

Figure 10:
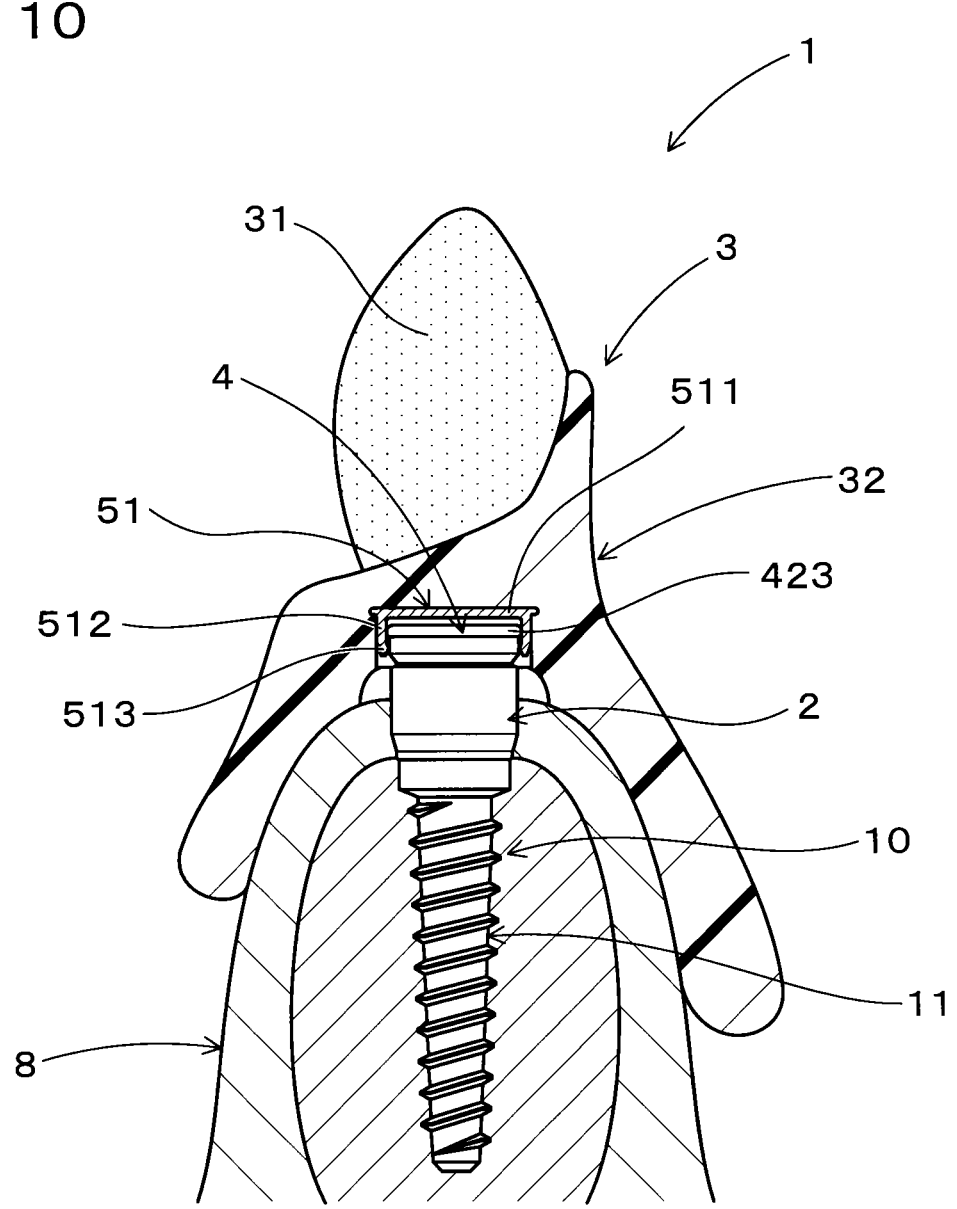
FIG. 10 is a sectional view of an implant overdenture system having a cap member according to Example 4.

In the implant overdenture system 1, as illustrated in FIG. 10, the magnetic assembly 4 is provided in the denture base 32 with a cap member 51 interposed therebetween.

The cap member 51 is formed from a synthetic resin, and has a disc-shaped cap body 511, and a cylindrical cap-side retainer 512 formed downward from an outer peripheral edge of the cap body 511. Provided at an opening end part of the cap-side retainer 512 is a retainer flange 513 extending inward. The retainer flange 513 is engageable with the flange 423 of the magnetic assembly 4.

The cap-side retainer 512 has an axial length greater than the thickness of the flange 423. The magnetic assembly 4 is axially movable to and from the retainer flange 513 and the lower surface of the cap body 511 on the inner side of the cap-side retainer 512.

Any other technical features are similar to Example 1.

In the implant overdenture system 1 of this example, the magnetic assembly 4 provided in the denture base 32 with the cap member 51 interposed therebetween is axially movable. Consequently, the whole implant overdenture 3 including the cap member 51 inserted therein is allowed to move relative to the implants 10 to which the implant overdenture 3 is fixed.

The keeper 2 and the magnetic assembly 4 may constantly abut each other at the same position. Still, the whole implant overdenture 3 including the cap member 51 held therein is allowed to positionally change relative to the keeper 2 within the area where the lower surface of the cap body 511 and the retainer flange 513 are located. A patient's gingiva is likely to undergo chronological changes such as a change in shape. The implant overdenture 3 thus movable can adjust its mounting position according to such chronological changes. This lessens the needs for reconditioning and/or repair conventionally required for the implant overdenture 3.

This example can attain effects similar to Example 1.

Example 5

This example presents another modified structure of the implant overdenture system 1.

Figure 11:
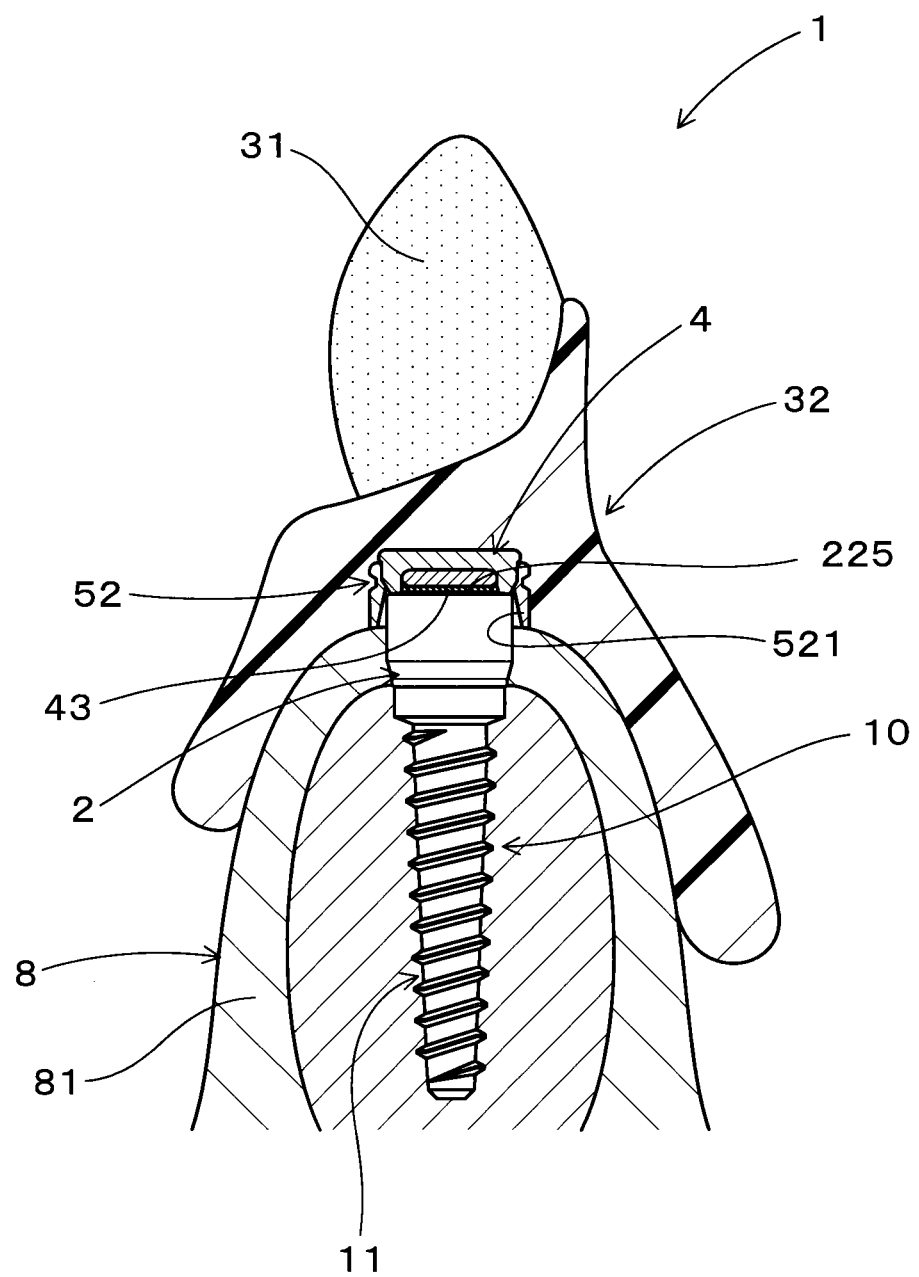
FIG. 11 is a sectional view of an implant overdenture system having a sleeve according to Example 5.

In the implant overdenture system 1, as illustrated in FIG. 11, a sleeve 52 formed from a metal such as a non-magnetic stainless steel is provided in the denture base 32 of the implant overdenture 3.

The sleeve 52 has a substantially cylindrical overall shape, and an opening end part of the sleeve 52 is situated so as to cover the outer peripheral surface of the magnetic assembly 4. The other opening end part of the sleeve 52 is protruding farther than the attractive surface 43 of the magnetic assembly 4. Formed at the other opening end part is a keeper locating fallen portion 521 that can accept therein the keeper 2 when the implant overdenture 3 is mounted onto the alveolar ridge 8.

Any other technical features are similar to Example 1.

In the implant overdenture system 1 of this example, the magnetic assembly 4 with the sleeve 52 attached thereto is inserted in the denture base 32 of the implant overdenture 3. The keeper 2 is fitted in the keeper locating fallen portion 521 encompassed by the sleeve 52 and the attractive surface 43, and the attractive surface 43 on the edge of the magnetic assembly 4 and the surface-to-be-attracted 225 of the keeper 2 fixedly abut each other. In the described state, the sleeve 52 is encompassing the outer peripheral side surface of the keeper 2.

As described above, the sleeve 52 is a metallic member. Therefore, the sleeve 52 encompassing the outer peripheral side surface of the keeper 2 serves to counteract a relative turning force that may be generated in a direction where the abutting surfaces of the keeper 2 and the magnetic assembly 4 (attractive surface 43 and surface-to-be-attracted 225) are obliquely torn off from each other. As compared to the conventional structures, therefore, the fall-out possibility of the implant overdenture 3 is more effectively controlled.

A plastic material may be used to form the sleeve 52. In that case, if a force is laterally applied to the implant overdenture 3, side-slip between the keeper 2 and the magnetic assembly is allowed by a clearance between the sleeve 52 and the keeper 2 and in a range of elastic deformation of the sleeve 52. This side-slip alleviates the laterally applied force.

This example can attain effects similar to Example 1.

Example 6

This example presents modified shapes of the surface-to-be-attracted 225 of the keeper 2 and the attractive surface 43 of the magnetic assembly 4 in the implant overdenture system 1 of Example 1.

Figure 12:
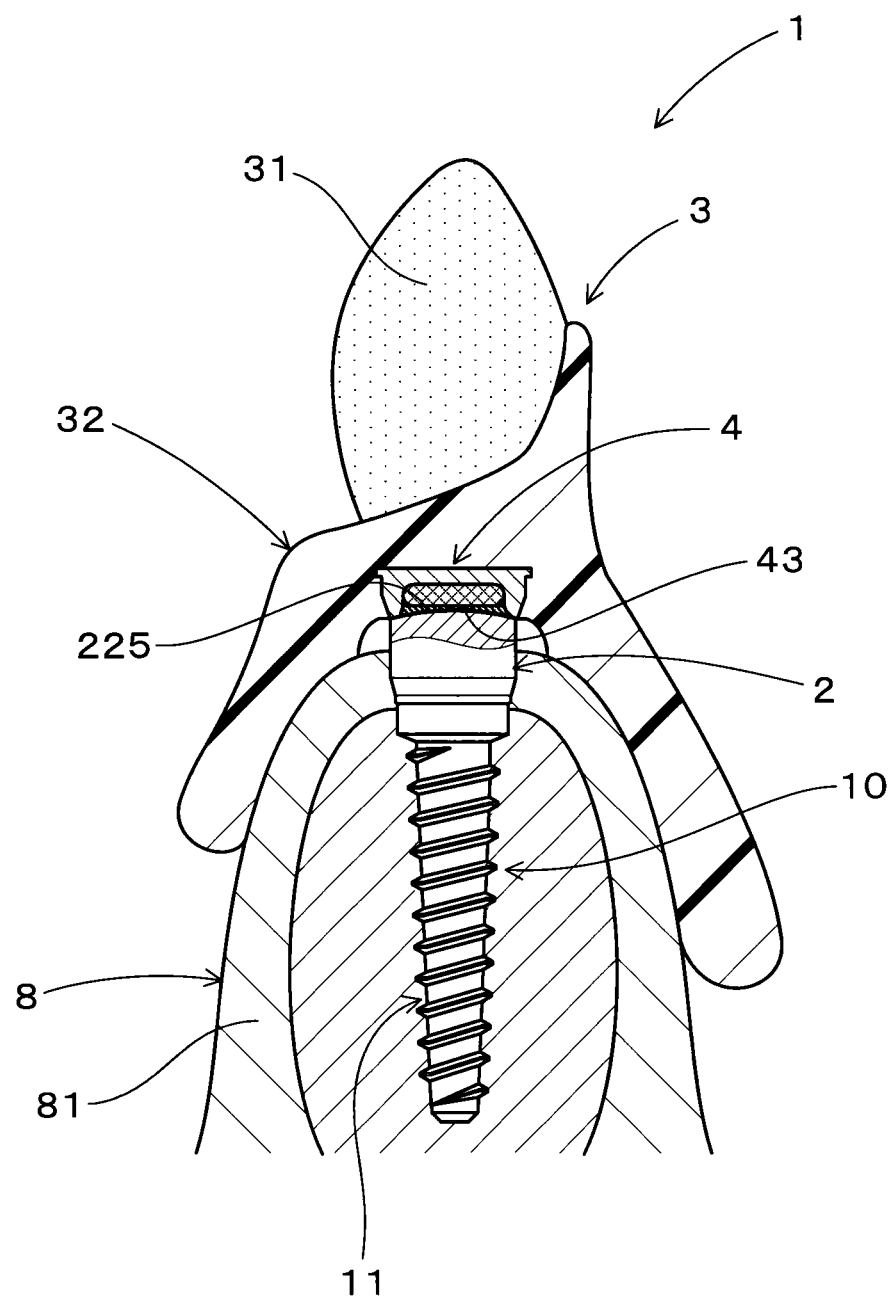
FIG. 12 is a sectional view of an implant overdenture system wherein abutting surfaces have spherical shapes according to Example 6.
Figure 13A:
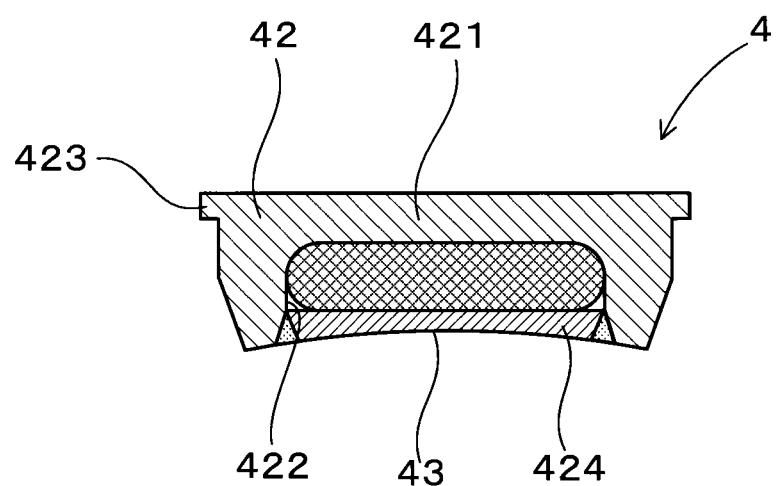
FIG. 13 (a) is a sectional view of a magnetic assembly.
FIG. 13(b) is a partial sectional view of a keeper according to Example 6.
Figure 13B:
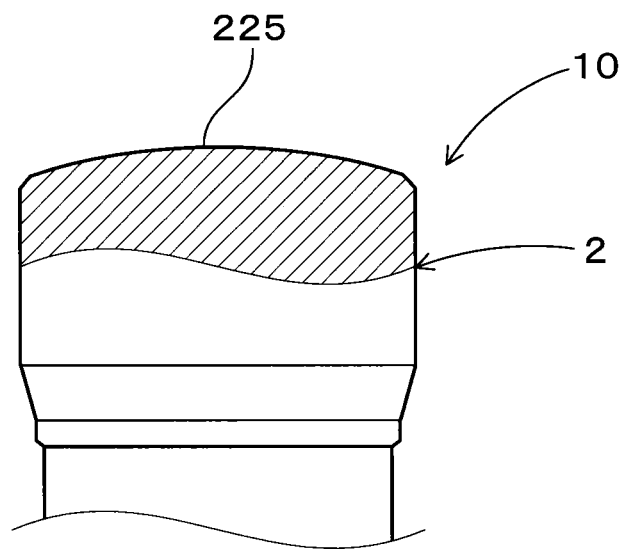

As illustrated in FIGS. 12 and 13 (*b*), the surface-to-be-attracted 225 of the keeper 2 has a bulging spherical shape.

On the other hand, the attractive surface 43 of the magnetic assembly 4 is formed in a recessed spherical shape correspondingly to the surface-to-be-attracted 225 of the keeper 2.

Any other technical features are similar to Example 1.

In the implant overdenture system 1 of this example, the attractive surface 43 of the magnetic assembly 4 is spherically recessed correspondingly to the spherically surface-to-be-attracted 225 of the keeper 2. The magnetic assembly 4 and the keeper 2 are accordingly tightly fitted to each other. This minimizes an air gap in the magnetic circuit, promising a sufficient magnetic attractive force.

The spherically bulging surface-to-be-attracted 225 and the correspondingly spherically recessed attractive surface 43 serve to impart rotatability between the keeper 2 and the magnetic assembly 4. This allows the implant overdenture 3 to oscillate and/or turn relative to the keeper 2 without providing any gap between the keeper 2 and the magnetic assembly 4, enabling the implant overdenture 3 to flexibly accommodate to a patient's occlusal habits.

This example can attain effects similar to Example 1.

Figure 14:
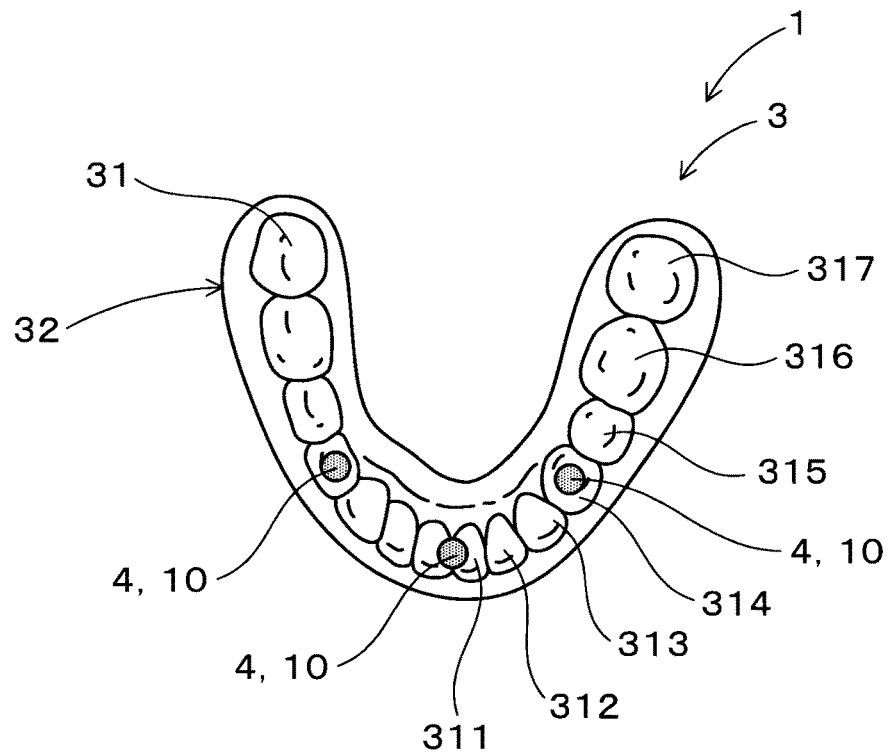
FIG. 14 is a drawing illustrating a layout example of the implants and the magnetic assemblies.
Figure 15:
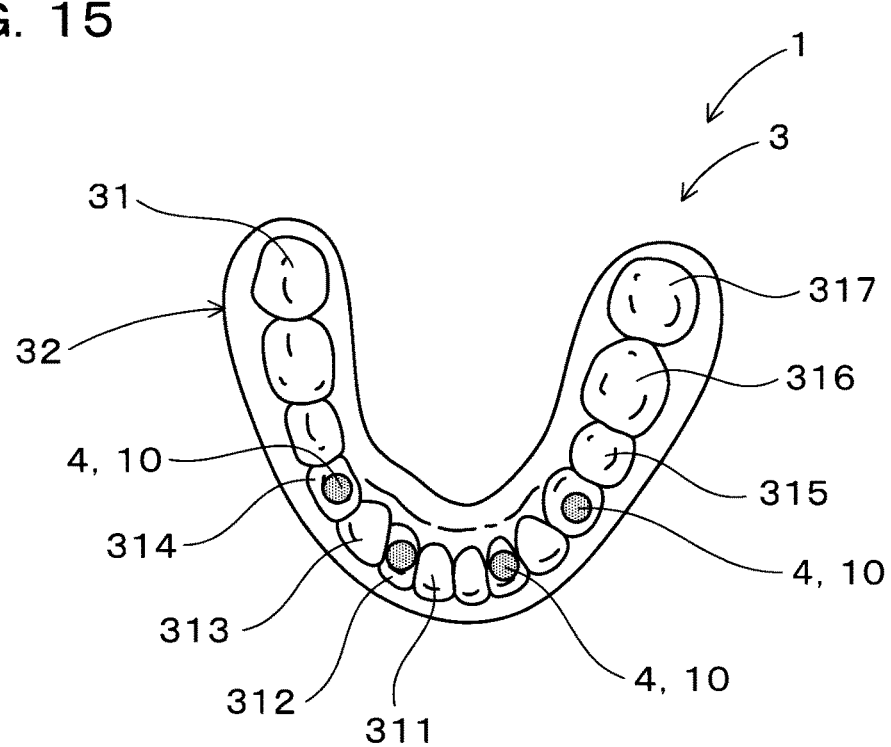
FIG. 15 is a drawing illustrating another layout example of the implants and the magnetic assemblies.

The examples 1 to 6 presented two implants 10 and two magnetic assemblies 4; however, more than two implants 10 and magnetic assemblies 4 may be provided. FIGS. 14 and 15 respectively illustrate an example with three implants 10 and three magnetic assemblies 4, and another example with four implants 10 and four magnetic assemblies 4.

In the case of providing three implants 10 and three magnetic assemblies 4, as illustrated in FIG. 14, one of them may be located at a position situated correspondingly to an intermediate position between the two central incisors 311, with the other two at positions located correspondingly to the left and right first premolars 314. In the case of odd numbers of implants 10 and magnetic assemblies 4, preferably, one of them may be located at a position situated correspondingly to an intermediate position between the two central incisors substantially at the center, with the rest of them respectively located at bilaterally symmetrical positions.

In the case of providing four implants 10 and four magnetic assemblies 4, as illustrated in FIG. 15, two of them may be located at a position situated correspondingly to the left and right lateral incisors 312, with the other two located at positions situated correspondingly to the left and right first premolars 314.

There are a lot of nerves running in regions of the alveolar ridge from the second premolars to the second molars. Therefore, the implants are preferably planted in a region of the alveolar ridge from the central incisors to the first premolars. The implants are more preferably planted in a region of the alveolar ridge from the central incisors to the canines.

The examples described so far presented just a few exemplified positions of the implants 10 and magnetic assemblies 4. The implants 10 and magnetic assemblies 4 may be located at variously different positions. Any positions that are roughly linearly symmetrical to the median line may be defined as bilaterally symmetrical positions.

Example 7

This presents an example of the implant overdenture system 1 used in a case where natural teeth remain on alveolar ridge 8.

Figure 16:
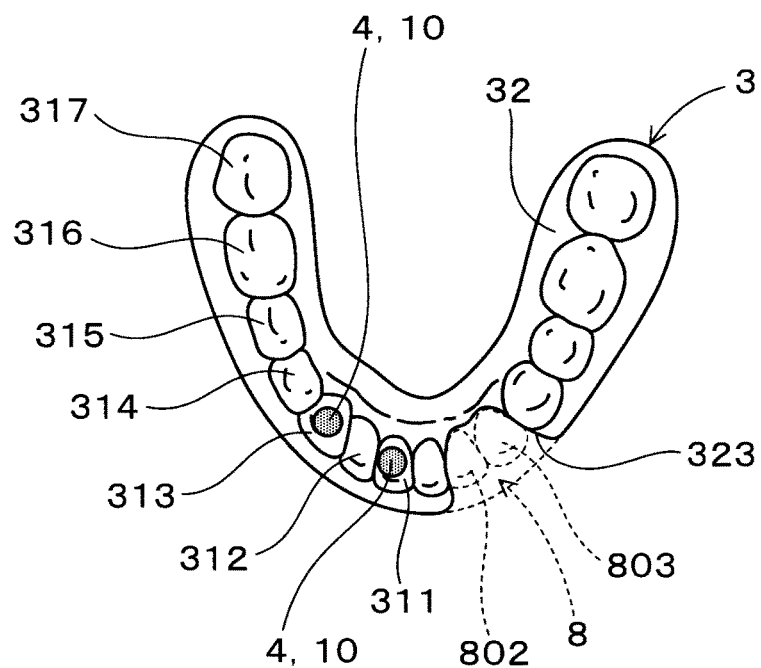
FIG. 16 is a drawing illustrating an implant overdenture system according to Example 7.

As illustrated in FIG. 16, this alveolar ridge 8 has two remaining teeth on the left side: lateral incisor 802 and canine 803.

As illustrated in FIG. 16, the denture base 32 of the implant overdenture 3 has a receding portion 323 formed by cutting out the denture base 32 at positions coincident with the remaining teeth (802, 803). The denture base 32, therefore, lacks the artificial teeth 31 for the lateral incisor 312 and the canine 313 on the left side. The receding portion 323 has an opening formed outward so as to accommodate therein the remaining teeth (802, 803).

As illustrated in FIG. 16, the magnetic assemblies 4 are inserted at positions of the artificial teeth 31 of the denture base 32 coincident with the central incisor 311 and the canine 313 on the right side. In this example, the magnetic assemblies 4 are situated at positions substantially bilaterally symmetrical to the remaining teeth on the left side: lateral incisor 802 and canine 803.

As illustrated in FIG. 16, the implants 10 are planted at positions in the alveolar ridge 8 located correspondingly to the magnetic assemblies 4 inserted in the implant overdenture 3.

Any other technical features are similar to Example 1.

This example can attain effects similar to Example 1.

Example 8

This presents an example of the implant overdenture system 1 for partial use on the alveolar ridge 8.

Figure 17:
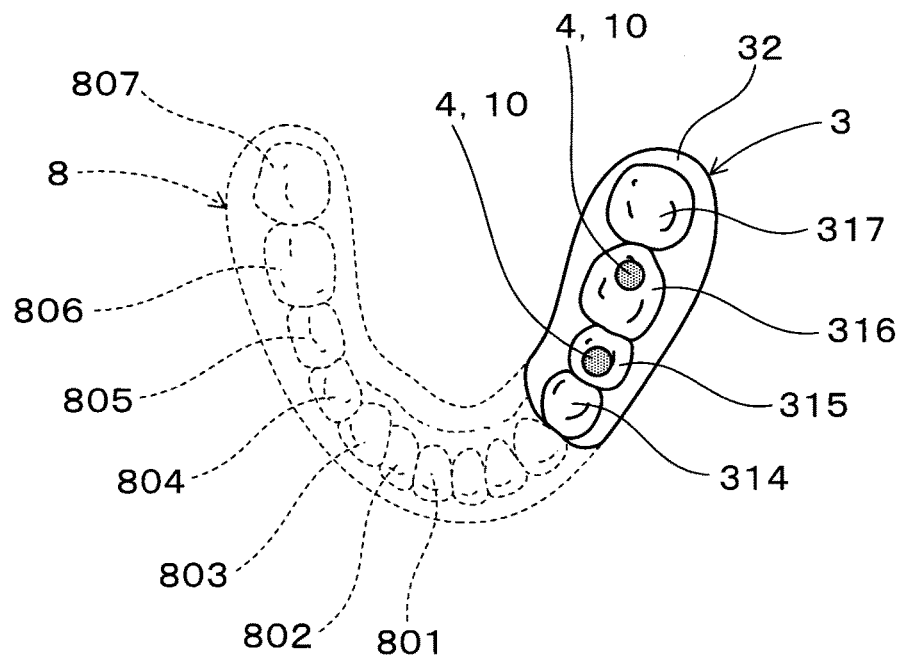
FIG. 17 is a drawing illustrating an implant overdenture system according to Example 8.

As illustrated in FIG. 17, the alveolar ridge 8 has 10 remaining teeth; central incisor 801, lateral incisor 802, canine 803, first premolar 804, second premolar 805, first molar 806, and second molar 807 on the right side, and central incisor 801, lateral incisor 802, and canine 803 on the left side.

As illustrated in FIG. 17, the denture base 32 of the implant overdenture 3 is formed in such a shape that covers a region of the alveolar ridge 8 where the natural teeth have been extracted. The denture base 8 has four artificial teeth 31; first premolar 314, second premolar 315, first molar 316, and second molar 317. The magnetic assemblies 4 are inserted at positions of the artificial teeth 31 of the denture base 32 coincident with the second premolar 315 and the first molar 316 on the right side.

As illustrated in FIG. 17, the implants 10 are planted at positions in the alveolar ridge 8 which are located correspondingly to the magnetic assemblies 4 inserted in the implant overdenture 3.

In this example, the magnetic assemblies 4 and the implants 10 are located at positions linearly symmetrical to a reference line, where the reference line is a straight line passing through a substantially central position in the longitudinal direction of the implant overdenture 3 and orthogonal to the longitudinal direction.

Any other technical features are similar to Example 1.

This example can attain effects similar to Example 1.

The invention claimed is:

1. An implant system for fixing an implant overdenture onto alveolar ridge, comprising:
a magnetic assembly including at least one magnet configured to be provided in the implant overdenture, the magnetic assembly having an attractive surface;
an implant body formed from a non-magnetic material and including threads formed on an outer peripheral side of the implant body to be inserted in a jawbone of the alveolar ridge; and
a keeper formed from a magnetic material and configured to be exposed from the alveolar ridge, the keeper including an upper surface portion and a side wall portion extending down from the upper surface portion and ending in a bottom face that is on an opposite side of the keeper from the upper surface portion, a fallen insert portion being included in the side wall portion the keeper having a surface-to-be-attracted at an upper face of the upper surface portion, the surface-to-be attracted not including any holes, the keeper constituting a magnetic circuit with the magnetic assembly provided in the implant overdenture when the attractive surface of the magnetic assembly and the surface-to-be-attracted of the keeper contact each other by a magnetic attractive force, wherein
a circumscribed circle diameter d1 in an outer shape of the surface-to-be-attracted of the keeper is equal to or larger than φ1.8 mm
a largest diameter d2 of an inserted part of the implant body inserted in jawbone is equal to or larger than φ1.2 mm and equal to or less than φ3.0 mm,
the circumscribed circle diameter d1 and the largest diameter d2 have a relationship expressed by d1/d2≤1.5,
the implant body comprises a solid insert portion extending above the threads formed on the outer peripheral side of the implant body to protrude from the inserted part of the implant body inserted in the jawbone, the solid insert portion not including any holes,
the implant body includes a flange extending outward from a top of a portion of the implant body that includes the threads,
the fallen insert portion of the keeper accepts therein the solid insert portion of the implant body,
the solid insert portion is inserted in the fallen insert portion to fix the implant body and the keeper to each other, and
a top face of the flange of the implant body faces and is in direct contact with the bottom face of the side wall portion of the keeper wherein the implant body, including the threads and the solid insert portion, is a single piece.

2. The implant system according to claim 1, wherein the implant is structured to fix the implant body and the keeper to each other by press-fitting the solid insert portion into the fallen insert portion.

3. The implant system according to claim 1, wherein
the solid insert portion has an external thread portion with threads formed on an outer peripheral side surface thereof,
the fallen insert portion has an internal thread portion with threads formed on an inner peripheral side surface thereof, and
the implant body and the keeper are fixed by engaging the external thread portion of the solid insert portion and the internal thread portion of the fallen insert portion with each other.

4. The implant system according to claim 2, wherein an outer peripheral side surface of the keeper is formed so as to be engaged with a tool for inserting the implant in the alveolar ridge.

5. The implant system according to claim 3, wherein the solid insert portion of the implant body comprises a fastening-engaging portion that is configured to be engaged with a tool for inserting the implant body in the alveolar ridge.

6. The implant system according to claim 1, wherein the flange of the implant body is positioned between the threads of the implant body and the keeper.

7. The implant system according to claim 1, wherein the fallen insert portion is an inner peripheral surface of the side wall portion,
the keeper includes an inner peripheral flange extending inward from the fallen insert portion, and
a largest diameter of the solid insert portion accepted within the keeper is larger than a diameter of the an inner peripheral flange of the keeper such that the solid insert portion is inserted in the fallen insert portion and directly contacts the fallen insert portion to fix the implant body and the keeper to each other.

8. The implant system according to claim 1, wherein the upper surface portion of the keeper has a bulging spherical shape and a corresponding surface of the magnetic assembly has a recessed spherical shape.

9. The implant system according to claim 1, wherein the upper surface portion of the keeper has a flat shape and a corresponding surface of the magnetic assembly has a flat shape.

* * * * *